(12) United States Patent  
Acker et al.

(10) Patent No.: US 7,762,253 B2
(45) Date of Patent: Jul. 27, 2010

(54) MULTIPLE LUMEN MONITORED DRUG DELIVERY NASAL CANNULA SYSTEM

(75) Inventors: Jaron M. Acker, Madison, WI (US); Jennifer L. Pakter, Verona, WI (US); Robert Q. Tham, Middleton, WI (US)

(73) Assignee: General Electric Company, Schenectady, NY (US)

( * ) Notice: Subject to any disclaimer, the term of this patent is extended or adjusted under 35 U.S.C. 154(b) by 436 days.

(21) Appl. No.: 11/299,935

(22) Filed: Dec. 12, 2005

(65) Prior Publication Data

US 2007/0135757 A1 Jun. 14, 2007

(51) Int. Cl.
*A61M 16/00* (2006.01)
*A61M 39/00* (2006.01)

(52) U.S. Cl. .................. 128/204.26; 128/204.23; 128/207.18; 128/204.18; 128/203.12; 128/202.27

(58) Field of Classification Search ............ 128/200.24, 128/203.12, 204.18, 204.22, 207.18, DIG. 26, 128/911
See application file for complete search history.

(56) References Cited

U.S. PATENT DOCUMENTS

| | | | | |
|---|---|---|---|---|
| 3,314,294 A * | 4/1967 | Colston | ...................... | 137/804 |
| 4,054,133 A * | 10/1977 | Myers | ................... | 128/204.26 |
| 4,106,505 A * | 8/1978 | Salter et al. | ............ | 128/207.18 |
| 4,846,791 A * | 7/1989 | Hattler et al. | ................. | 604/43 |
| 4,883,051 A * | 11/1989 | Westenskow et al. | .. | 128/204.21 |
| 5,029,580 A * | 7/1991 | Radford et al. | ........ | 128/207.14 |
| 5,190,520 A * | 3/1993 | Fenton et al. | .................. | 604/43 |
| 5,195,962 A * | 3/1993 | Martin et al. | .................. | 604/43 |
| 5,603,315 A * | 2/1997 | Sasso, Jr. | ............... | 128/204.18 |
| 6,089,105 A * | 7/2000 | Ricciardelli | .............. | 73/861.52 |
| 6,089,229 A * | 7/2000 | Bathe et al. | ............ | 128/204.21 |
| 6,634,360 B1 * | 10/2003 | Flodin | ................... | 128/207.14 |
| 6,668,828 B1 * | 12/2003 | Figley et al. | ........... | 128/204.18 |
| 7,305,988 B2 * | 12/2007 | Acker et al. | ........... | 128/204.18 |
| 2002/0017300 A1 | 2/2002 | Hickle et al. | | |
| 2003/0226566 A1 * | 12/2003 | Dhuper et al. | ......... | 128/207.15 |
| 2004/0097965 A1 * | 5/2004 | Gardeski et al. | ............ | 606/129 |
| 2004/0194781 A1 * | 10/2004 | Fukunaga et al. | ...... | 128/203.12 |
| 2007/0028924 A1 * | 2/2007 | Madsen et al. | ......... | 128/207.15 |
| 2007/0028925 A1 * | 2/2007 | Madsen et al. | ......... | 128/207.15 |

* cited by examiner

*Primary Examiner*—Justine R Yu
*Assistant Examiner*—Clinton Ostrup
(74) *Attorney, Agent, or Firm*—Andrus, Sceales, Starke & Sawall, LLP

(57) ABSTRACT

A multiple lumen nasal cannula that can be used to delivery two separate supplies of gases to a patient. The multiple lumen nasal cannula includes a first lumen for delivering a first gas and a second lumen for delivering a second gas. The first lumen includes support structure that reduces the tendency of the cannula to kink and lock the delivery of gas to a patient. The cannula assembly includes a mixing chamber positioned near the patient such that the two supplies of gas are not mixed until a location approximate to delivery to the patient. The nasal cannula assembly includes a connecting device that allows the two separate supplies of gas to be correctly delivered to the two different lumens of the nasal cannula.

11 Claims, 10 Drawing Sheets

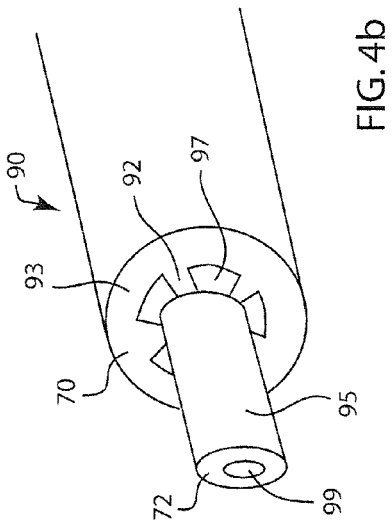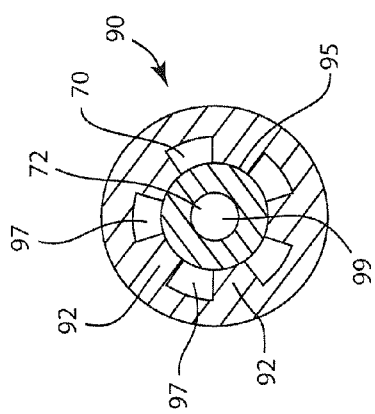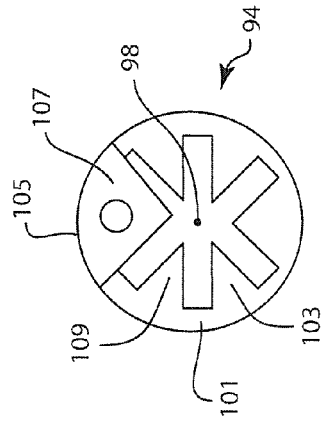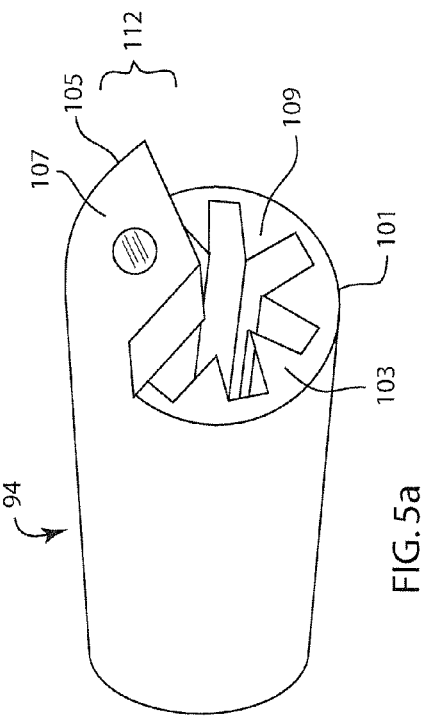

MULTIPLE LUMEN MONITORED DRUG DELIVERY NASAL CANNULA SYSTEM

FIELD OF THE INVENTION

The present invention relates to a medical device for providing medical gasses from at least one gas source to a patient. More specifically, the present invention relates to a multiple lumen cannula for delivering multiple medical gasses to a patient and mixing the gasses at a location proximal to the patient.

BACKGROUND OF THE INVENTION

Patients that have respiratory difficulties often must be placed on a mechanical ventilator. These difficulties may be pathological in nature or may be due to the fact that a patient is too weak or sedated to independently proper respiration functions. Often, the patient may be spontaneously attempting to breathe but not able to complete a full respiratory cycle. In these cases mechanically assisted ventilation is provided. In mechanically assisted ventilation a combination and pressure and/or flow sensors detect a patient's breath attempt. This detection triggers the delivery of a mechanical breath. This breath is provided by the delivery of a pulse or plug of medical gases under a pressure that is sufficient to overcome the resistance of the patient's airway to fill the lungs. When this pulse of medical gas is discontinued the natural compliance of the patient's chest wall forces the delivered breath out of the patient in an expiratory phase.

Mechanical ventilation can comprise the delivery of air, but often the breath that is delivered is formed of a mixture of various medical gasses. These gasses may include oxygen, helium, nitric oxide (NO), a drug aerosol, or, in the case of anesthesia delivery, an anesthetic agent. The proper combination of medical gasses would be decided upon by the clinician in response to the ailments of the patient.

Efficient mechanical ventilation requires a quality ventilator-patient interface. This requires a quality seal around the patient airway thereby providing efficient delivery of the medical gasses. There are many varieties of ventilator-patient interfaces. These varieties include face masks which cover the patient's mouth and nose, an endotracheal tube, or a nasal cannula. While there are advantages to each of the patient interfaces a nasal cannula presents the advantage of providing a higher quality connection to the patient's respiratory system than a face mask while being less invasive than an endotracheal tube.

In the delivery of some medical gasses to a patient it is desirable to keep the gasses separate until shortly before they are delivered to the patient. This may arise due to properties desired in each of the gasses, structural components of the mechanical ventilator, or because of adverse reactions between different medical gasses. One example of such adverse reactions is the reaction that takes place when oxygen is mixed with nitric oxide. Nitric oxide is a gas that, when inhaled, acts to dilate blood vessels in the lungs, improving oxygenation of the blood and reducing pulmonary hypertension. Therefore it is often desired to deliver a combination of nitric oxide to improve lung function with an increased concentration of oxygen to improve oxygen transfer. However, oxygen and nitric oxide react to form nitrogen dioxide ($NO_2$), a toxic substance. Therefore, to reduce the production of nitric oxide it is desirable to keep the supply of oxygen and nitric oxide separate until just before it is delivered to the patient.

In many clinical or critical care situations a patient is connected to a wide variety of monitoring and/or support devices. These devices may include patient monitoring such as ECG, EMG, or EEG, fluid and/or nutritional support in the form of a catheter, patient waste removal, or respiratory support in the form of a mechanical ventilator. A challenge arises with this multitude of patient connections in keeping them tangle free and properly connected to the patient. This becomes difficult when the patient is moving, clinicians are moving about the patient, or the patient (and connected equipment) must be moved within the treatment facility. While data connections are more susceptible to disconnection from the patient gasses or fluid delivery connections are susceptible to kinks or entanglements in the lines resulting in restricted or interrupted delivery to the patient.

Therefore it is desirable in the field of mechanical ventilation to provide a kink resistant nasal cannula that can separately deliver multiple medical gasses to a location proximal to a patient.

SUMMARY OF THE INVENTION

In general, the present invention provides a kink resistant delivery means for medical gasses. A nasal cannula is provided with multiple lumens for the separate delivery of multiple medical gases. More specifically, a second lumen is disposed within a first lumen to provide for multiple medical gasses and additional structures within the cannula to provide kink resistance.

An additional aspect of the present invention comprises the monitoring of each of the medical gasses within the nasal cannula. This monitoring detects the pressure within the lumen of the medical gas being delivered to the patient. This pressure may be monitored as a differential pressure between the multiple lumens of the nasal cannula. As a further aspect of the present invention, the differential pressure measurement may be used to determine the state of the medical gas delivery to the patient via the nasal cannula. This state may include the detection of normal operation, a kink in the nasal cannula, or disconnection of the ventilator-patient interface.

In another aspect of the present invention, the patient triggering means or means for detecting a patient breath attempt may be disposed within the nasal cannula to provide more accurate detection of patient breath attempts and triggering of the delivery of pulses of medical gas to the patient.

In a still further aspect of the present invention, the multiple lumen cannula of the present invention comprises a mixing chamber disposed at one end of the cannula proximal to the patient interface. The mixing chamber provides for the mixing of medical gasses at a location proximal to the patient for delivery to the patient.

In a final aspect of the nasal cannula of the present invention, the nasal cannula comprises a connection assembly that facilitates the connection of the sources of medical gas to the multiple lumen cannula of the present invention. This connection assembly provides the low resistance delivery of the medical gasses from their source to the multiple lumens of the cannula. The connection means for each lumen of the multiple lumen cannula is morphologically different thus insuring the proper connection of the multiple lumens of the cannula.

BRIEF DESCRIPTION OF THE DRAWINGS

FIG. 4a is an end view of the coaxial dual lumen cannula of a first embodiment of the invention;

FIG. 4b is a perspective view of the coaxial dual lumen cannula;

FIG. 5a is a perspective view of a dual lumen cannula of a second embodiment of the invention;

FIG. 5b is an end view of the dual lumen cannula shown in FIG. 5a;

DETAILED DESCRIPTION

Figure 1:
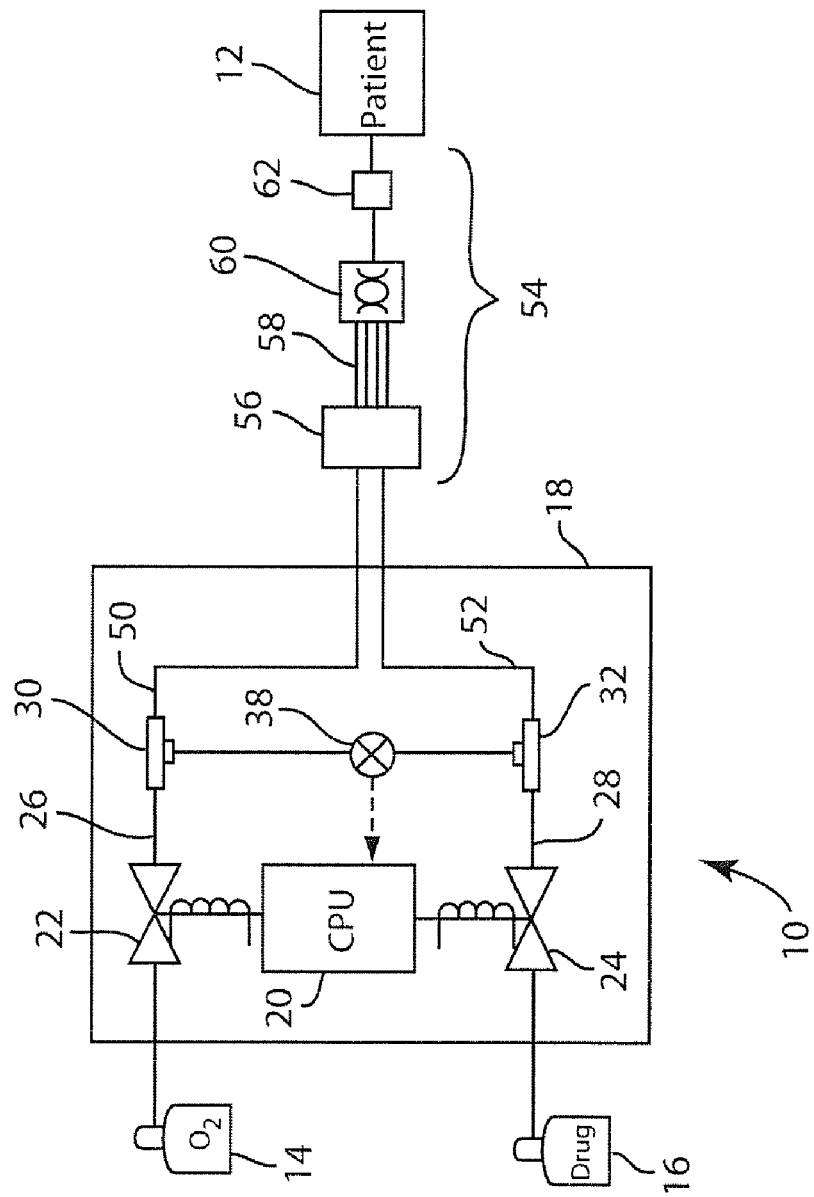
FIG. 1 is a schematic diagram of the ventilator system of the present invention.

Referring to FIG. 1, a ventilator system 10 for delivering one or more medical gasses to a patient 12 is shown. The ventilator system 10 delivers a quantity of medical gas from supply tanks 14 and 16 to a patient 12 via a mechanical ventilator 18. The medical gases in supply tanks 14 and 16 may comprise, but are not limited to, air, oxygen, nitrogen dioxide ($NO_2$) helium, and a drug aerosol. Within the mechanical ventilator 18 is a CPU 20 that controls the electrical and mechanical components of the mechanical ventilator 18, including a first valve 22 and a second valve 24 disposed within conduits 26 and 28 respectively to control the flow of medical gas from supply tanks 14 and 16. In an embodiment of the present invention, first valve 22 and second valve 24 may be solenoid valves but it is understood that any valve with the suitable time response to control medical gas flow may be used. First t-connector 30 and second t-connector 32 are disposed along conduits 26 and 28 respectively and provide a connection via conduits 34 and 26 respectively to differential pressure transducer 38. Differential pressure transducer 38 relays the differential pressure information to CPU 20 via electrical connection 40. CPU 20 may use this differential pressure data to control elements of the mechanical ventilator 18 including the ventilator engine 42 via electrical connection 44, first valve 22 via electrical connection 46, and second valve 24 via electrical connection 48.

After first t-connector 30 and second t-connector 32, the medical gasses travel via conduit 50 and 52 respectively to cannula assembly 54. The cannula assembly 54 generally includes a connection assembly 56, a cannula 58, a mixing chamber 60 and patient interface 62. The conduits 50 and 52 connect to connection assembly 56 of the cannula assembly 54. Connection assembly 56 supplies the medical gas from the conduits 50 and 52 to the first and second lumens of cannula 58, the details of which will be discussed below. Cannula 58 may be approximately two meters in length to provide adequate gas connection between the patient 12 and the mechanical ventilator 18 with a suitable range of motion and connection. The gas mixing chamber 60 is disposed at the end of cannula 58 proximal to the patient 12. Within gas mixing chamber 60, the first and second lumens of the cannula 58 provide the gaseous connection to facilitate the mixing of the two previously separate medical gasses. Gas mixing chamber 60 allows for the medical gasses to be delivered to patient 12 via patient interface means 62 as a homogenous mixture. Patient interface means 62 in the present embodiment comprises a nasal cannula, but it is understood that alternative patient interface means may be used, including a face mask or an endotracheal tube.

Figure 2:
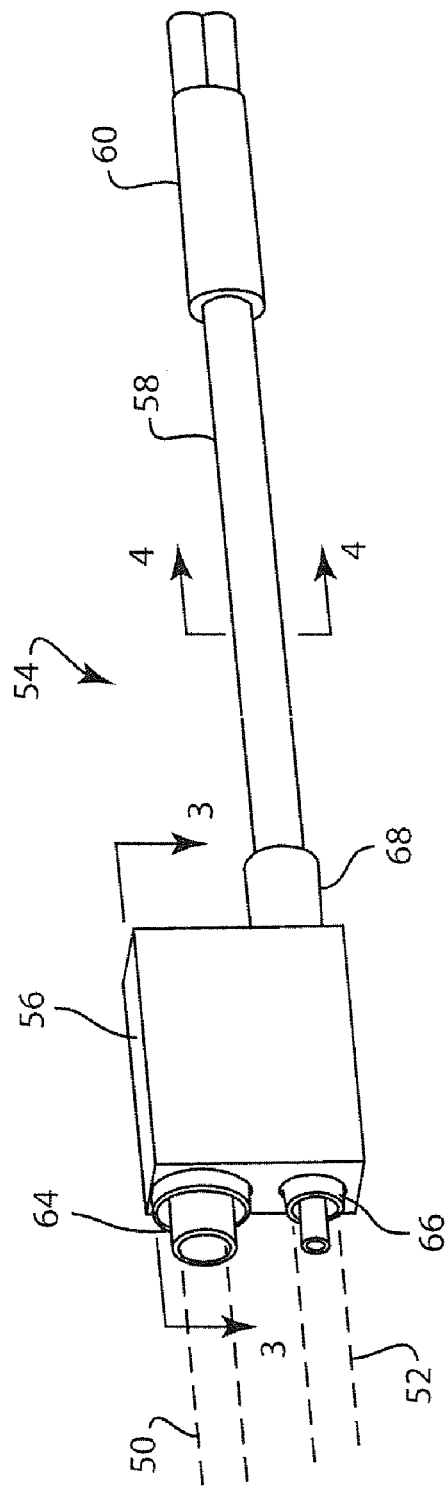
FIG. 2 is a perspective view of the cannula assembly of the present invention.

Referring to FIG. 2, cannula assembly 54 comprises connection assembly 56, cannula 58, and gas mixing assembly 60. Medical gas is supplied to connection assembly 56 via conduits 50 and 52. Conduits 50 and 52 are respectively attached to first supply port 64 and second supply port 66 of the connection assembly 56. Connection assembly 56 is connected to cannula 58 via a cannula supply port 68.

Figure 3:
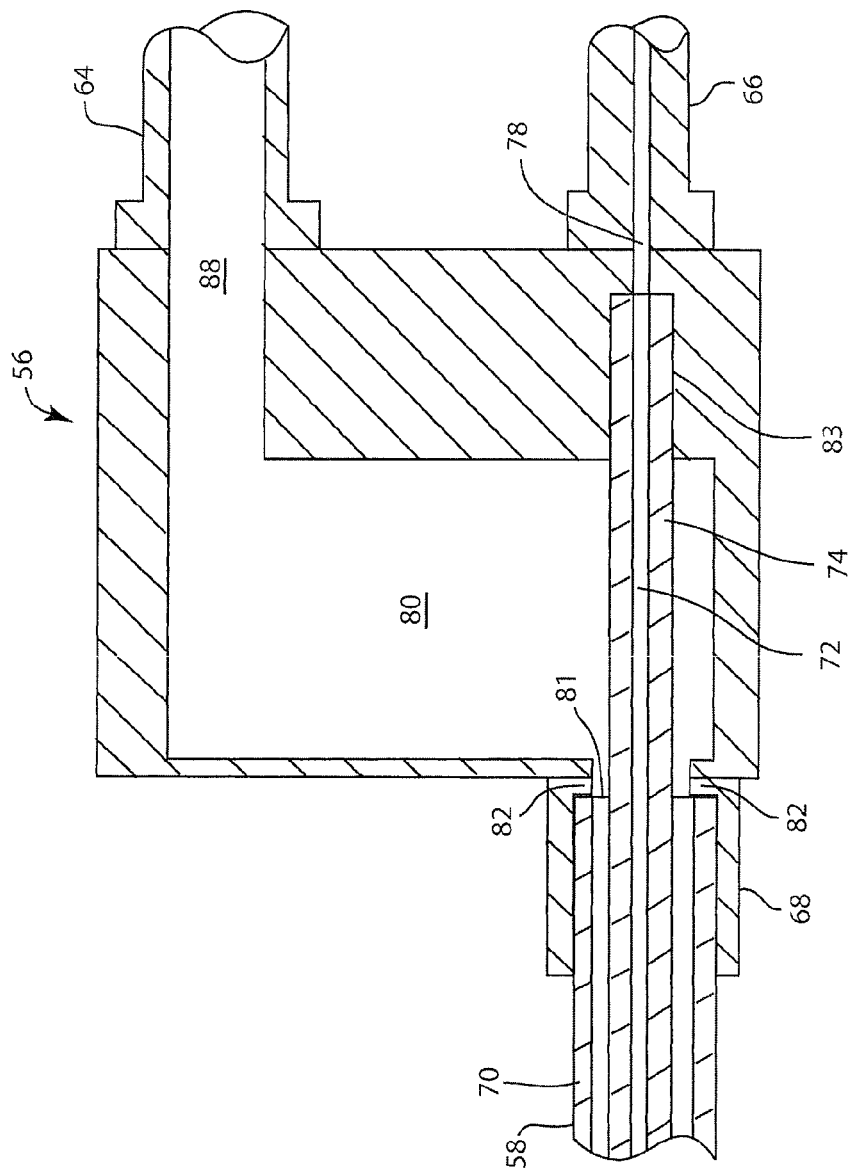
FIG. 3 is a section view taking along line 3-3 of FIG. 2 illustrating the connection assembly.

FIG. 3 illustrates a section view of the connection assembly taken along line 3-3 of FIG. 2. As illustrated in FIG. 3, the connection assembly 56 includes a first supply port 64 that receives the oxygen conduit 50 and the second supply port 66 that receives the gas conduit 52. The first supply port 64 directs the supply of oxygen into the lumen chamber 80 through the passageway 88. The lumen chamber 80 is in fluid communication with the annular supply port 68, which receives the cannula 58.

The second supply port 66 receives the therapeutic gas and directs the gas to an internal passageway 83 that receives an extended portion of the cannula 58 in a manner to be described in great detail below.

In the preferred embodiment of the invention, the connection assembly 56 is formed from PVC, which is appropriate for transmitting medical gases. However, other appropriate materials could be utilized while operating with the scope of the present invention.

The multiple lumen design 90 of a first embodiment of the present invention can be seen in FIG. 4 with a first outer lumen 70 and disposed within it a second lumen 72. FIG. 4b depicts the first lumen 70 stripped away from second lumen 72 to facilitate proper insertion of the dual-lumen cannula 90 into cannula supply port 68. Referring back to FIG. 3, upon insertion of cannula into cannula supply port 68, the extended portion 74 of second lumen 72 extends through lumen chamber 80 to conduit 78 leading from second supply port 66. The extended portion 75 is sealed within the passageway 83, such as with a solvent bond, to provide a gaseous connection from supply tank to second lumen 72.

As extended portion 74 extends into the passageway 83, the leading edge 81 of the first lumen 70 is disposed within cannula supply port 68 until the leading edge 81 abuts the annular ring 82. The first lumen 70 is sealingly connected to the cannula supply port 68 by means of an adhesive, such as a solvent bond. Annular ring 82 provides an additional seal between connection assembly 56 and cannula 58 while allowing for a gaseous connection between first lumen 70 and lumen chamber 80. As can be understood in FIG. 3, the medical gas, such as oxygen, from the supply tank is supplied to the lumen chamber 80 by the first supply port 64 and the passageway 88. The medical gas flows through the lumen chamber 80 and into the first, outer lumen 70 through the opening defined by the annular ring 82. The second, therapeutic drug is supplied to the connection assembly 56 through the second supply port 66 and passes through the conduit 78. The second gas enters the extended portion 74 of the second, inner lumen 72 such that the two separate supplies of gases can be delivered to the respective inner and outer lumens 70, 72.

Referring back to FIG. 2, the dual lumen cannula 58 provides the gaseous connection between connection assembly 56 and gas mixing chamber 60. As depicted in the cross-section view of FIG. 4, the cannula 90 may comprise a coaxial design. In the coaxial multiple lumen cannula 90, kink resistance and structural support is provided by a plurality of ridges 92 that extend from the outer wall 93 of the first lumen 70 to the outer wall 95 of the second lumen 72. These ridges 92 are preferably made of the same PVC material as the rest of the cannula 58.

As can be understood in FIGS. 4a and 4b, the outer lumen 70 includes a series of flow passageways 97 positioned between the series of ridges 92. The flow passageways 97 provide an area for the gas to flow between the first lumen 70 and the second lumen 72. The second lumen 72 includes a center passageway 99 that allows gases to flow through the second lumen 72. In the first embodiment shown in FIGS. 4a and 4b, the flow passageways 97 and center passageway 99 are coaxial.

In the dual-lumen cannula 90 depicted in FIG. 4, the cross-sectional area of the center passageway 99 of the second lumen 72 and the combined area of the series of flow passageways 97 contained within the outer lumen 70 are selected based upon the flow rate of the gases being delivered through each of the first and second lumens 70,72. The flow area within each of the first and second lumens is proportional to the lumen resistance, which in turn is proportional to the gas flow through the lumen. In order to equalize the pressure differential between the first and second lumens, the flow area included in each of the lumens is selected to produce a very small pressure differential during typical gas flow rates. For example, if the gas flow rate through the center passageway 99 is significantly less than the flow rate through the series of flow passageways 97, the flow area of the center passageway 99 should be small to create approximately the same back pressure as the outer lumen 70. The selection of the flow areas allows a differential pressure sensor to be used to monitor the pressures within the first and second lumens 70,72.

Referring now to FIG. 5, the cannula 94 may alternatively comprise a double lumen cannula design in which the lumens are not coaxial. The double lumen cannula 94 comprises a first lumen 101 with an outer wall 103 and a second lumen 105 with an outer wall 107. However, as opposed to the coaxial multiple lumen cannula discussed previously, in the double lumen cannula 94, the first lumen 101 and the second lumen 105 share a portion of their outer walls 103 and 107, respectively, so that the first lumen 101 and second lumen 105 are in a parallel relationship along the length of the cannula 94. The double lumen cannula 94 of the second embodiment provides the same structural and kink resistance properties as the coaxial multiple lumen cannula 90. The kink resistance and structural support of the double lumen cannula 94 is supplied by a thicker outer wall of the second lumen 105, as well as by the plurality of ridges 109 that extend from the outer wall of the first lumen 101 towards the central axis 98, as shown in FIG. 5b.

As discussed above, the flow areas contained within the first lumen 101 and the second lumen 105 are selected to create an equal back pressure for the preferred gas flow rates through both of the first and second lumens 101,105. The matching pressures within the first and second lumens 103, 105 allow a differential pressure sensor to be utilized to monitor the flow through the double lumen cannula 94.

Figure 6B:
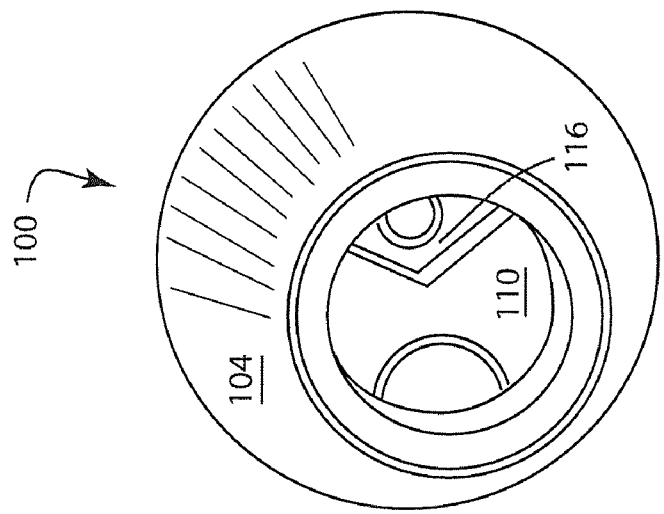
FIGS. 6a and 6b illustrate a connection assembly for the second embodiment of the dual lumen cannula.
Figure 6A:
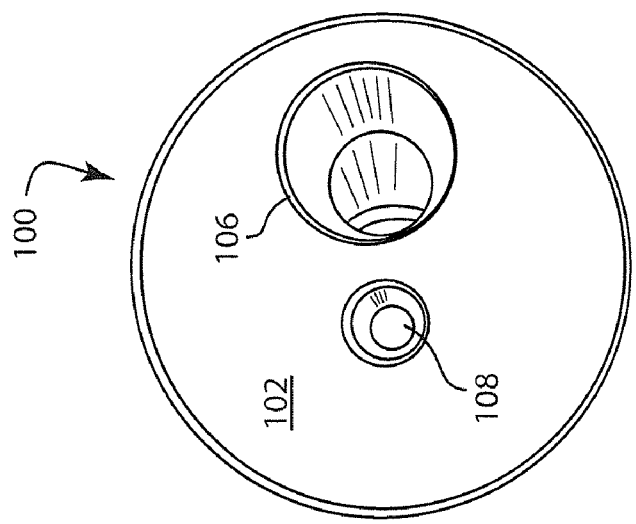

The double lumen cannula 94 shown in FIG. 5 utilizes an alternative connection assembly 100, depicted in FIG. 6, rather than the connection assembly 56 for use with coaxial multiple lumen cannula 90. Connection assembly 100 is depicted in FIG. 6 with FIG. 6a depicting the ventilator side 102 and FIG. 6b depicting the patient side 104 of connection assembly 100. Ventilator side 102 comprises a first supply port 106 for gaseous connection with conduit 50 and a second supply port 108 for gaseous connection with conduit 52. Patient side 104 of connection assembly 100 comprises a cannula supply port 110. However, because the double lumen cannula 94 has an asymmetrical cross section, the potential exists for misconnection of the double lumen cannula 94 to the cannula supply port 110. Therefore, as depicted in FIG. 5b, the outer wall 107 of second lumen 105 comprises a morphologically different region 112 at the ventilator connection end of the double lumen cannula 94. The morphologically different region 112 is complementary to morphologically different receptor 116 formed in the connection assembly 100. The complementary nature of morphologically distinctive receptor 116 thus insures that the ventilator end of double lumen cannula 94 may only be connected to connection assembly 100 in a single, proper orientation.

Figure 7:
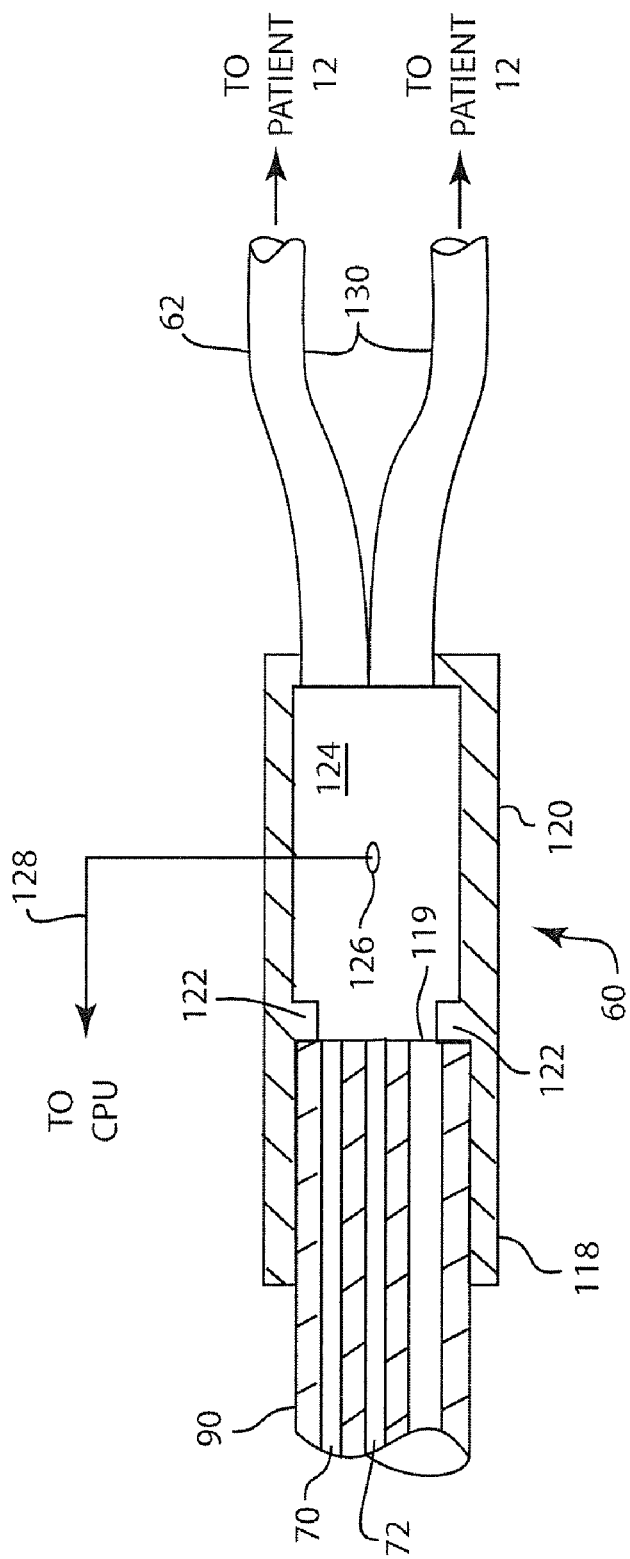
FIG. 7 is a section view of the gas mixing chamber attached to the cannula of the present invention.

Referring now to FIGS. 2 and 7, the cannula 58, which in FIG. 7 is depicted as coaxial multiple lumen cannula 90, is inserted into ventilator end 118 of gas mixing assembly 60. The cannula 90 is inserted until its outer end 119 abuts annular ring 122, which separates the ventilator end 118 from the patient end 120 of the gas mixing assembly 60. Patient end 120 of gas mixing assembly 60 includes a mixing chamber 124 for the mixing of the medical gasses separately supplied by first lumen 70 and the second lumen 72. The mixing assembly 60 allows the gasses to remain separate until a location proximate to the patient wherein a homogenous mixture of the medical gasses may be formed just prior to delivery to the patient via a patient connection means 62. In FIG. 7, the connecting means 62 is shown as a nasal cannula; however it is understood that alternative suitable patient connection means may also be used.

In a further aspect of the invention, a patient trigger sensor 126 may be disposed within mixing chamber 124 so that in the absence of gas flow through either of the nasal cannula lumens, a patient trigger may be detected. This provides a location proximate to the patient for the detection of a patient breath attempt, is used to trigger the delivery of a breath of medical gas from the ventilator, which would then be supplemented with a pulse of medical gas from supply tanks 14 and/or 16. The detection of this patient trigger would be sent along connection 128 to CPU 20 to facilitate the control over the ventilator system 10. Alternatively, the patient trigger sensor 126 may be disposed within one or both of the nasal cannulas 130. In the absence of gas flow through one of the nasal cannula channels, that particular lumen is used to measure the pressure in the mixing chamber or end of the cannula. The pressure at the base of the alternate gas tube is measuring the pressure at the point of the t-connector. In a further aspect of the present invention, the patient trigger sensor 126 may be replaced by an additional function by differential pressure transducer 38 wherein the differential pressure detected by differential pressure transducer 38 is used to detect the patient breathing attempt trigger when there is an absence of gas flow through either of the nasal cannula lumens 70 and 74 respectively.

Figure 8A:
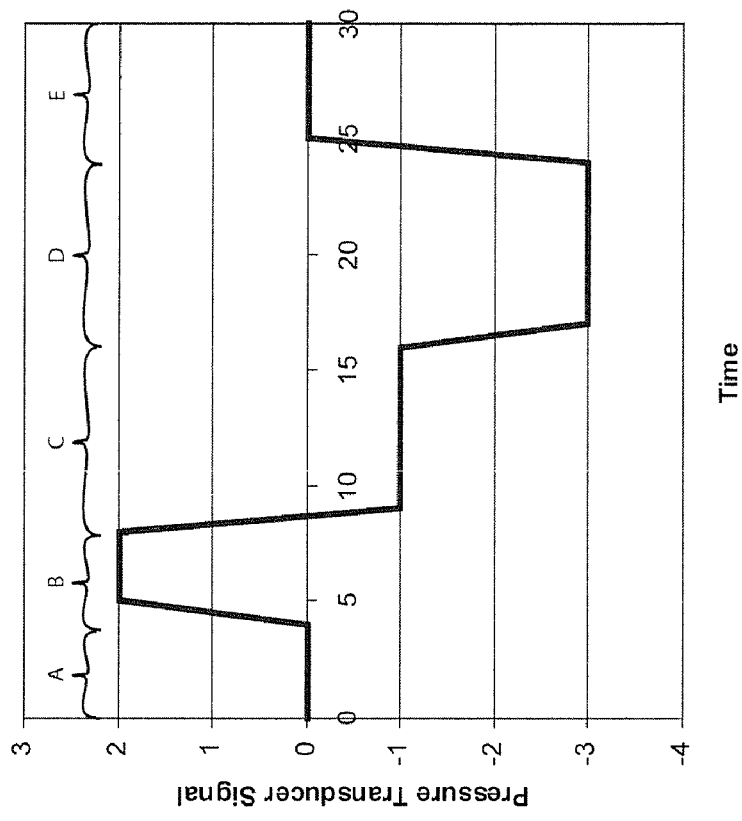
FIGS. 8a-8d are graphs representative of the pressure change sequence that may be detected within the cannula of the present invention.

In another aspect of the present invention, the differential pressure transducer 38 may provide data for the monitoring of the connection and/or gas flow within the cannula 56 of the present invention. As depicted in FIGS. 8a-d, deviations from a normal or expected gas flow or pressure profile would be indicative of inadequate flow, cannula disconnection, or cannula kinking. FIG. 8a depicts the normal, expected differential pressure profile within the gas mixing chamber 60 of the cannula assembly 54. The gasses are delivered through first and second lumens at their different patterns, therefore the differential pressure profile exhibits five regions a-d in a differential pressure detection cycle. Regions a and e are representative of when there is no gas flow being supplied from supply tanks 14 or 16. Region b is representative of the period when a proper gas flow is being supplied by supply tank 14 to the patient. This gas supply continues throughout region c as well, but in region c proper gas supply from supply tank 16 is also provided thereby producing the shift in differential pressure within the gas mixing chamber 60. In region d, the pulse of medical gas supplied from supply tank 14 has ceased and as such the only medical gas supply is that supplied from supply tank 16 as the differential pressure indicates. Finally in region e both pulses of medical gas from the supply tanks 14 and 16 have ceased and no differential pressure in the gas mixing chamber 60 is sensed by differential pressure transducer 38.

Figure 8B:
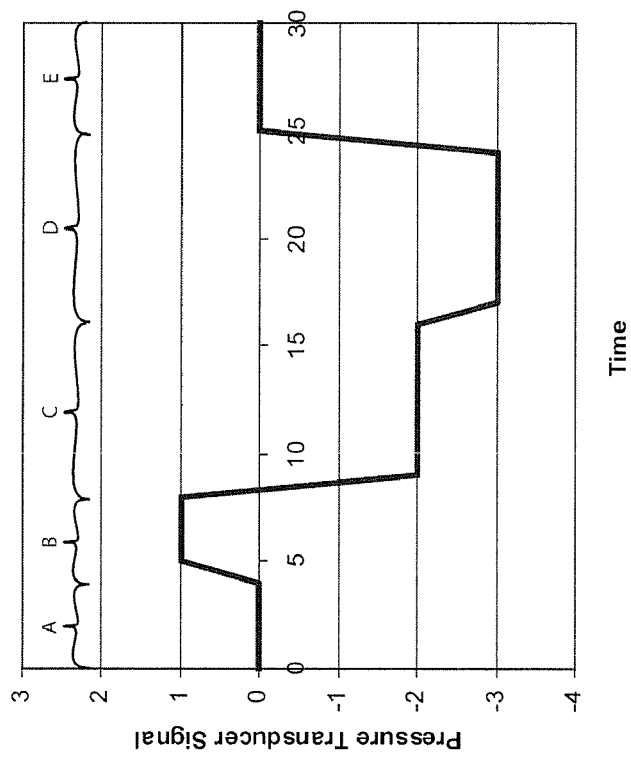

FIG. 8b depicts the differential pressure profile that would be indicative of an alarm condition and/or system failure because of inadequate gas flow through one or both of the lumens. When the pulse of medical gas in the first lumen begins to flow in region b, the signal from the differential pressure transducer is only half the amplitude of that same portion of the cycle in FIG. 8a. Because the resistance within the cannula is assumed to be linear, it can be expected that only half the requested flow has been achieved. This indication is visible throughout the entire pulse of the first medical gas by the reduced differential pressure signal detected in regions b and c.

Figure 8C:
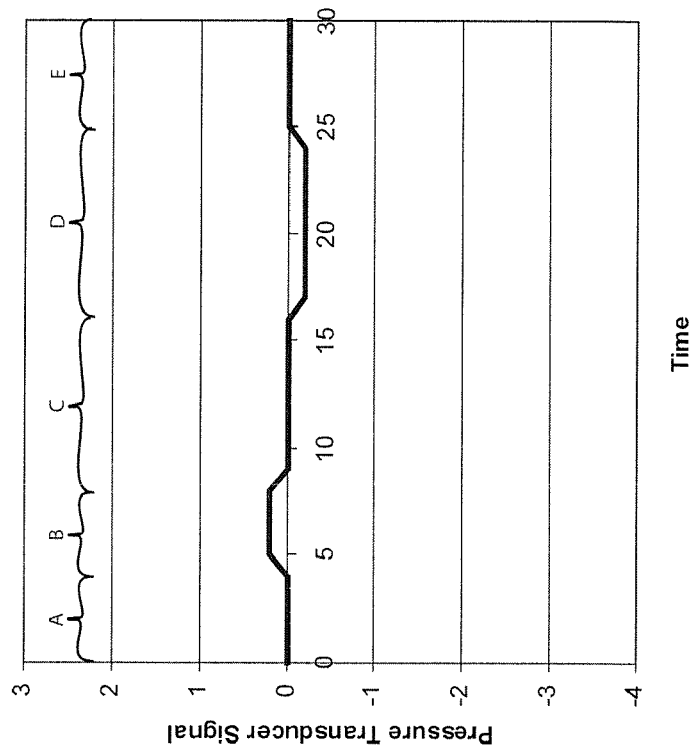

FIG. 8c depicts the differential pressure profile of the alarm condition of a disconnected nasal cannula. In FIG. 8c the same sequence of gas pulsing through the nasal cannula is present that was seen in FIGS. 8a and b; however, because of the near absence of back pressure when one or both of the nasal cannulas are disconnected, there is very little change in the signal during the gas pulsing. Therefore a differential pressure profile such as shown in FIG. 8c is indicative of a disconnected nasal cannula.

Figure 8D:
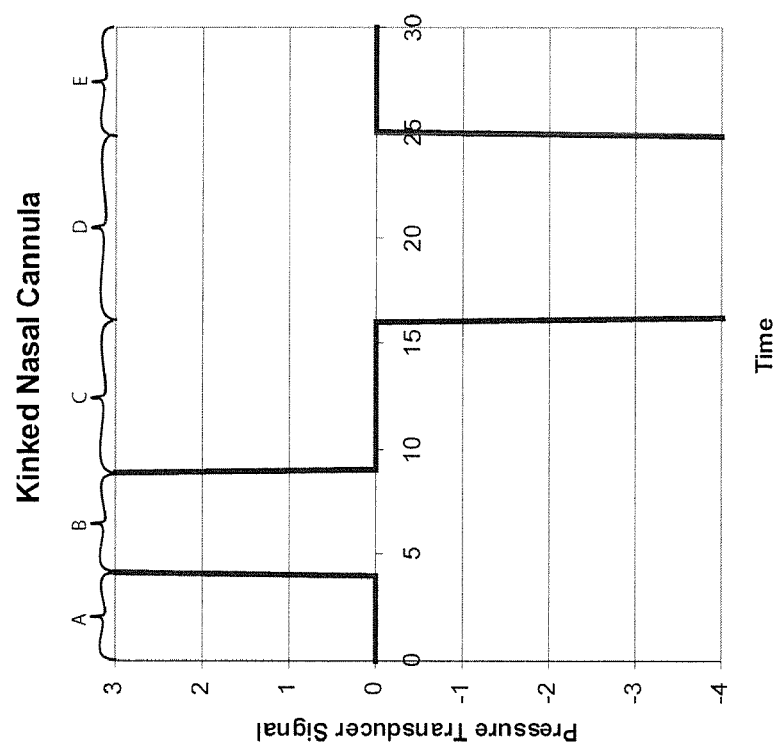

Finally in FIG. 8d another differential pressure profile indicative of the alarm condition of a kinked nasal cannula is shown. Once again, the differential pressure profile has the same sequence of gas pulses that are seen in the normal operation differential pressure profile; however, in the event of a kinked nasal cannula, the result will be a spike in the signal from the differential pressure transducer. The spike in the signal in region b is indicative of a kink in the first lumen and the spike in the signal in region d is indicative of a kink in the second lumen. Therefore, FIG. 8d depicts a complete kink of both the first and second lumens of the cannula of the present invention.

The differential pressure profile detected by the differential pressure transducer 38 thus provides a means for detecting a patient breath attempt thus triggering the delivery of a ventilator breath and pulses of supplemental medical gasses. The differential pressure transducer 38 also provides the additional functionality of monitoring the gas flow in the lumens of the multiple lumen cannula of the present invention as well as monitoring the quality of the patient connection to the cannula of the present invention.

What is claimed is:

1. A multiple lumen cannula assembly for delivery of multiple medical gasses to a patient, the multiple lumen cannula assembly comprising:
   a first lumen of a first cross-sectional area for the delivery of a first medical gas, the first lumen having a plurality of flow passages separated by a plurality of ridges;
   a second lumen of a second cross-sectional area disposed within the first lumen for the delivery of a second medical gas, wherein the first cross-sectional area is larger than the second cross-sectional area;
   a connection assembly comprising a first portion for providing the first medical gas to the plurality of flow passages of the first lumen and a second portion for providing the second medical gas to the second lumen;
   a mixing chamber located proximal to the patient and configured to receive the first medical gas from the first lumen and the second medical gas from the second lumen, wherein the mixing chamber combines the first and second medical gasses prior to delivery to the patient; and
   a patient triggering device disposed in the mixing chamber for detecting a patient breathing attempt; and
   a kink resistive means disposed between the plurality of flow passages of the first lumen, thereby providing structural support to the multiple lumen cannula,
   wherein the first lumen is defined between a first lumen wall and a second lumen wall and second lumen is defined by the second lumen wall and the kink resistive means comprises the plurality of ridges disposed between the plurality of flow passages within the first lumen, wherein each of the plurality of ridges extends from the first lumen wall defining the first lumen and contacts the second lumen wall defining the second lumen.

2. The multiple lumen cannula of claim 1 further comprising a differential pressure transducer for comparatively monitoring the gas flow in the first and second lumens.

3. The multiple lumen cannula of claim 2 wherein the differential pressure transducer can determine a state of flow representative of one of a plurality of conditions, the plurality of conditions including normal flow, inadequate flow of one of the medical gasses, a disconnected cannula, and, a kinked cannula.

4. The multiple lumen cannula of claim 1 wherein the first and second lumens are maintained in a coaxial relationship.

5. The multiple lumen cannula of claim 1 wherein the first lumen wall and the second lumen wall are coaxial.

6. The multiple lumen cannula of claim 5 wherein the second lumen wall is substantially thicker than the first lumen wall.

7. The multiple lumen cannula of claim 1 wherein the first medical gas delivered to the patient via the first lumen is $O_2$ gas and the second medical gas delivered to the patient via the second lumen is a drug aerosol.

8. The multiple lumen cannula of claim 1 wherein the cross-sectional area of the first lumen and the cross-sectional area of the second lumen are selected such that the gas pressure within the first lumen is approximately equal to the gas pressure within the second lumen during a desired flow rate of the first medical gas and a desired flow rate of the second medical gas.

9. The multiple lumen cannula of claim 1 further comprising: a gas monitoring device for monitoring the amount of medical gases being delivered to the patient by the first and second lumen.

10. A multiple lumen cannula assembly for delivery of multiple medical gases to a patient, the multiple lumen cannula assembly comprising:
    a connection assembly having a first supply port for receiving a first medical gas, a second supply port for receiving a second medical gas, and a cannula supply port;
    a first lumen of a first cross-sectional area in communication with the first supply port to receive the first medical gas, the first lumen having a plurality of flow passages defined between a first lumen wall and a second lumen wall;
    a second lumen of a second cross-sectional area defined by the second lumen wall and disposed within the first lumen and in communication with the second supply port to receive the second medical gas, wherein both the first lumen and the second lumen are received within the cannula supply port;

a mixing chamber located proximal to the patient and configured to receive the first medical gas from the first lumen and the second medical gas from the second lumen, wherein the mixing chamber combines the first and second medical gasses prior to delivery to the patient;

a patient triggering device disposed in the mixing chamber for detecting a patient breathing attempt; and a plurality of ridges disposed within the first lumen that extends from the first lumen wall of the first lumen into contact with the second lumen wall of the second lumen such that the plurality of ridges define the plurality of passages and provide structural support to the multiple lumen cannula to reduce kinking.

11. The multiple lumen cannula of claim 10 further comprising a differential pressure transducer positioned within the mixing chamber to comparatively monitor the gas flow in the first and second lumens.

\* \* \* \* \*